United States Patent [19]

Brothers

[11] Patent Number: 5,009,236
[45] Date of Patent: Apr. 23, 1991

[54] URINE COLLECTION SYSTEM

[76] Inventor: William S. Brothers, 1815 N. 1400 East, Provo, Utah 84604

[21] Appl. No.: 471,609

[22] Filed: Jan. 29, 1990

[51] Int. Cl.$^5$ .............................................. A61B 5/00
[52] U.S. Cl. .................................... 128/761; 128/762
[58] Field of Search ...................... 128/761, 762, 763; 604/408, 409, 410, 322; 383/13, 24, 25, 33, 63

[56] References Cited

U.S. PATENT DOCUMENTS

| | | | |
|---|---|---|---|
| 3,635,091 | 1/1972 | Linzer et al. | 128/761 X |
| 3,750,647 | 8/1973 | Gleason et al. | 128/762 X |
| 3,830,107 | 8/1974 | Linzer et al. | 128/761 X |
| 4,000,768 | 1/1977 | Siegel | 383/63 X |
| 4,626,249 | 12/1986 | Harney | 128/761 X |
| 4,680,808 | 7/1987 | Paleschuck | 383/9 |
| 4,696,067 | 9/1987 | Woodward | 128/761 X |

Primary Examiner—Steven A. Bratlie
Attorney, Agent, or Firm—M. Reid Russell

[57] ABSTRACT

A urine collection system that includes, in one embodiment, a mount with handle for manual positioning by a female, which mount includes fixed co-planer outwardly extending rods that are for receiving sleeves formed along edges of a mouth of a flexible bag, the rods to maintain the flexible bag mouth end spread open. The flexible bag includes a press to close type closure for sealing the bag mouth end after use.

In another embodiment the mount includes co-planer fixed outside rods with a co-planer sliding center rod installed therebetween, the sliding center rod for fitting through a center longitudinal slot that is formed through the mount handle and includes a finger engaging end for manual manipulation to slide the sliding rod from one side of the longitudinal slot to the other, which sliding center rod is for installation in a center sleeve that is formed above a junction at mouth edges of a pair of flexible bags, which flexible gabs also include sleeves formed along their outer mouth edges that are for fitting over the fixed outside rods. The flexible bags each include independent press to close type closures for individually sealing each bag.

8 Claims, 2 Drawing Sheets

URINE COLLECTION SYSTEM

BACKGROUND OF THE INVENTION

1. Field of the Invention

This invention relates generally to receptacles and particularly to urine specimen collection systems for females.

2. Prior Art

It is current medical practice to obtain from a patient a urine specimen or sample in a glass, plastic or fiber bottle or cup, such being capped and labeled for processing. Collection of a urine specimen in such vessel has a number of problems, particularly for a female, to include directing flow into the vessel, overflow, and the like.

While bottles and vessels are currently the usually used urine collection systems, heretofore several urine collection systems have been developed. A patent to Ersek, U.S. Pat. No. 3,346,883, shows an example of a flexible receptacle for arrangement on a toilet, and includes, adhesive layers. The Ersek receptacle provides a vessel that is unlike the bag collector of the present invention and does not include a holder for allowing a female to control bag positioning. Patents to Giesy, U.S. Pat. No. 3,335,714; Gleason, et al., U.S. Pat. No. 3,750,648; and Li, U.S. Pat. No. 4,023,216, all show examples of rigid funnel type devices, a mouth of each for positioning over the end of a female urethra, receiving urine therefrom that flows through a spout end into a collection vessel. Unlike the present invention, none of these systems utilizes a flexible sack with water tight closure and mount therefor, which mount includes a hand engaging end for manually positioning the open mouth of the flexible sack.

The present invention, in a second embodiment, is somewhat like a U.S. patent to Gleason, et al., in that they both recognize that it is sometimes required to collect two separate urine specimens. Gleason, et al., however, provides an arrangement of two separate collection bottles each receiving a discharge from an end of a split spout of a solid funnel. Unlike this arrangement, the present invention provides a pair of bags that are joined into a common top edge with separate outer edges. This second embodiment of the present invention provides a holder that allows a user to selectively open one bag mouth or the other.

SUMMARY OF THE INVENTION

It is a principal object of the present invention to provide a urine collection system that utilizes a flexible bag and holder therefore for use to conveniently collect a urine specimen from a human female.

Another object of the present invention is to provide a urine collection system for use by a human female that is sanitary to use, in that it includes a holder arrangement that is maintained out of the urine discharge path while positioning an open flexible bag in that discharge path, minimizing the likelihood that the user's hand will come in contact with the urine during use.

Another object of the present invention is to provide a urine collection system that utilizes sealable single use flexible plastic bags to minimize a likelihood of contamination of the collected specimen.

Still another object of the present invention in a urine collection system is to provide, in a second embodiment, an arrangement for collecting separate urine specimens during a single discharge, the specimens flowing into each of a pair of flexible bags, which bags are joined along a common edge that is mounted to a holder to be capable of selectively opening the mouth end of one bag and then the other.

In accordance with the above objects, the present invention is in a urine collection system that, in a first embodiment, consists of a flexible bag having a wide mouth that includes a press to close sealing arrangement, with sleeves formed along the opposite mouth edges. A mount of this embodiment includes a rectangular block end wherefrom co-planar rods extend from a leading block face or side. Which rods are slightly oppositely bowed and slope towards one another. The rods are to receive the flexible bag sleeves slid thereover.

In practice, the flexible bag is mounted on the rods with its open mouth facing upwardly as an extension of the block leading face or side, which block is for gripping by a female to appropriately position the bag open mouth. After use, the flexible bag sleeves are slid off the rods and the flexible bag mouth edges are pressed together, to seal the contents therein.

A second embodiment of a urine collection system of the present invention includes a holder that is arranged for mounting two flexible bags thereto that are joined together at a mouth edge of each for simultaneous collection of two urine specimens from a female. The flexible bags are joined along their inside mouth edges, and each bag is arranged for individual sealing. The common flexible bag mouth edges and the outside mouth edges each include sleeves formed therealong.

In the second embodiment, for selectively opening one flexible bag mouth or the other, a preferred mount consists of a rectangular block that includes, from one leading face or side thereof, co-planar fixed outside rods that are to receive the sleeves of the flexible bags outside mouth edges, slid thereover. A slot is formed longitudinally through the block and extending thereacross, the slot terminating proximate to the block sides. The slot is to receive a straight rod that is fitted therethrough and is to slide into the sleeve that is formed in the flexible bags common mouth edge. So arranged, with the straight rod positioned against one slot end, a flexible bag mouth diagonally therefrom is open and the other flexible mouth is closed, the flexible bags open and closed mouth relationship is reversed when the straight rod is moved across the block slot, into proximity with the other slot end.

DESCRIPTION OF THE DRAWINGS

The drawings illustrate that which is presently regarded as the best mode for carrying out the invention.

DETAILED DESCRIPTION

Figure 1:
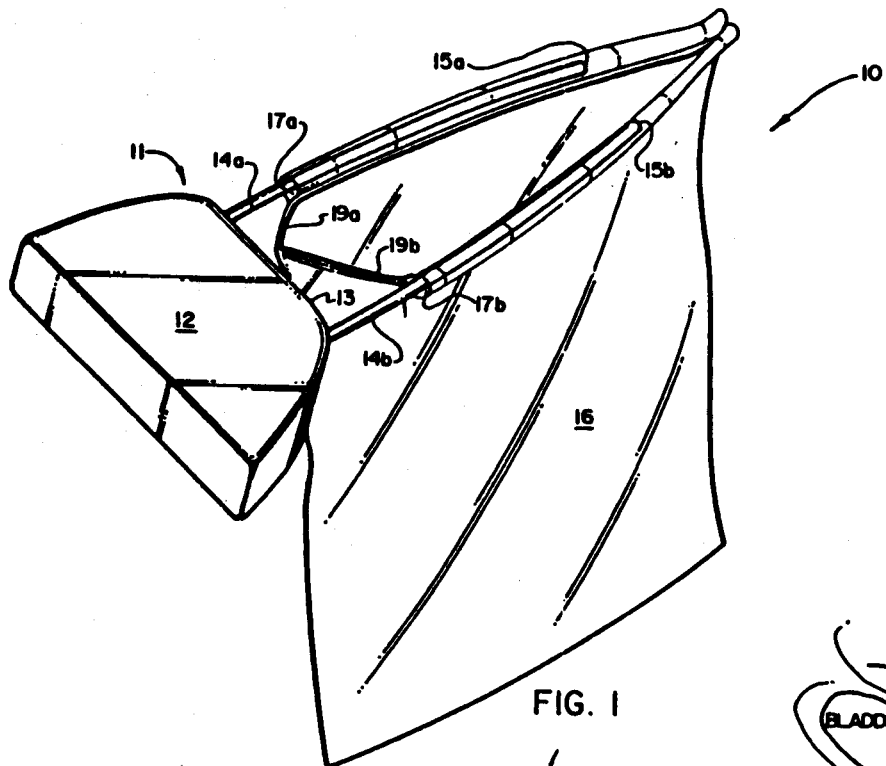
FIG. 1 is a profile perspective view taken from the top and right side of a first embodiment of a urine collection system of the present invention.
Figure 3:
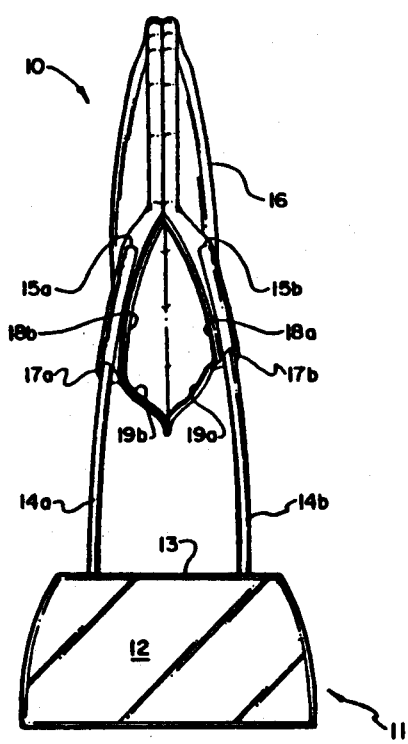
FIG. 3 is a top plan view of the flexible bag of FIG. 2, shown partially withdrawn off of bag mounting rods, the sides of the flexible bag mouth shown as having been pulled off from the bag mounting rod ends and are shown as having been squeezed together with a seal locking ridge pressed into a locking groove, sealing the mouth edges together.

In FIG. 1 is shown a first embodiment of the present invention in a urine collection system 10, hereinafter referred to as collector. Shown therein, the collector 10 includes a mount 11 that has a hand engaging rectangular block end 12 from one flat forward face or side 13 of which extend co-planar identical bag mounting rods 14a and 14b, hereinafter referred to as rods. Shown in FIGS. 1 and 3, the rods 14a and 14b are bent or curved inwardly from their connection to mount 11, with rod ends 15a and 15b shown as somewhat rounded. So arranged, the rounded rod ends, as shown best in FIG. 3, are for fitting into sleeves 17a and 17b that are formed along the mouth edges of a flexible bag 16. The flexible bag 16 is preferably formed from a plastic material like that being used in a conventional sealable sandwich bag. Like such sandwich bag, the flexible bag 16, as shown in FIGS. 1 and 3, preferably includes a ZIP LOCK™ type seal arranged below the sleeves 17a and 17b. The seal, as shown best in FIG. 3 preferably consists of a slot 18a that extends the length of one flexible bag mouth edge and is to receive and close around a ridge 18b that is formed along the length of the other flexible bag mouth edge, below sleeve 17b. So arranged, and aligning together and pressing of ridge 18b into slot 18a, along their length, provides a sealed closure of the mouth end of the flexible bag 16.

Figure 2:
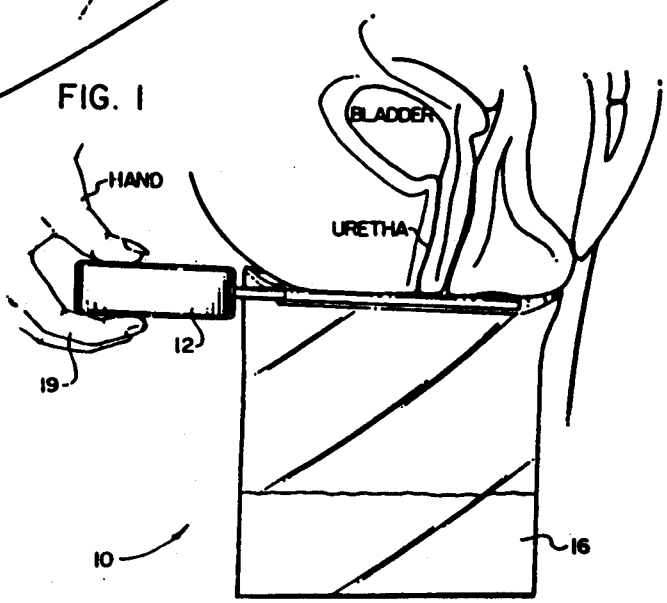
FIG. 2 is a side elevation view of a female patient holding a handle end of the urine collection system of FIG. 1, positioning an open mouth end of a flexible bag to receive a urine specimen therein.

FIG. 2 illustrates a use of collector 10 by a female who holds the rectangular block end 12 of mount 11 in her hand 19 for positioning flexible bag 16 open mouth end.

FIG. 3 shows the sleeves 17a and 17b of a portion of the flexible bag 16 as being pulled off from the rod ends 15a and 15b. Shown also, the portion of the seal slot 18a and ridge 18b being pressed together, sealing the one end of the open mouth of the flexible bag as it is removed off bag mounting rods 14a and 14b of mount 11, after collection of a specimen therein.

Figure 4:
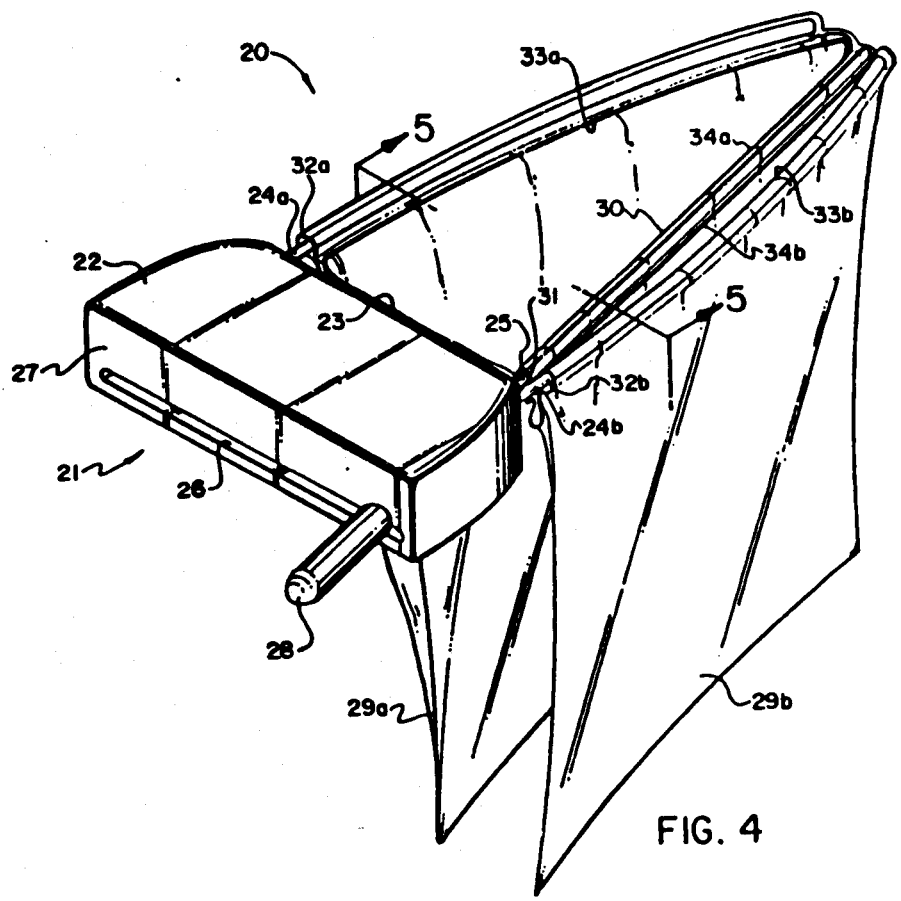
FIG. 4 shows a profile perspective view taken from the top and right side of a second embodiment of a urine collection system of the present invention.
Figure 5:
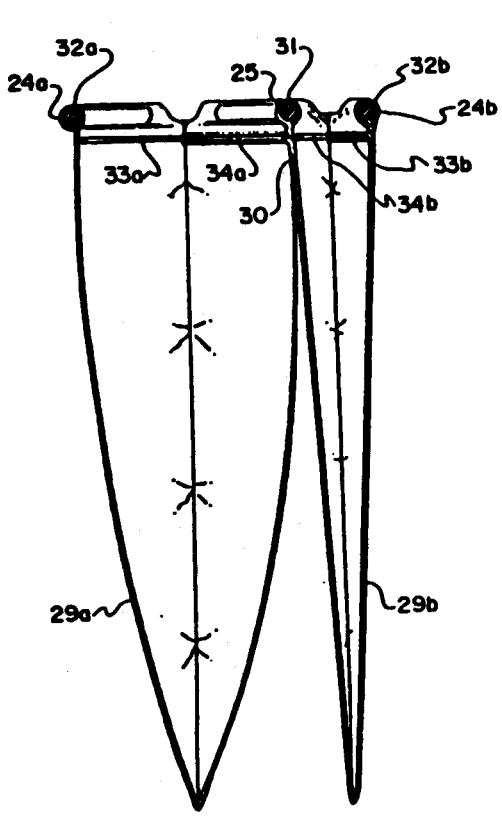
FIG. 5 is a sectional view taken along the line 5—5 of FIG. 4 showing the two flexible bags joined along a common mouth edge with a sleeve formed thereabove that contains a sliding center rod of a mount telescoped therethrough.
Figure 6:
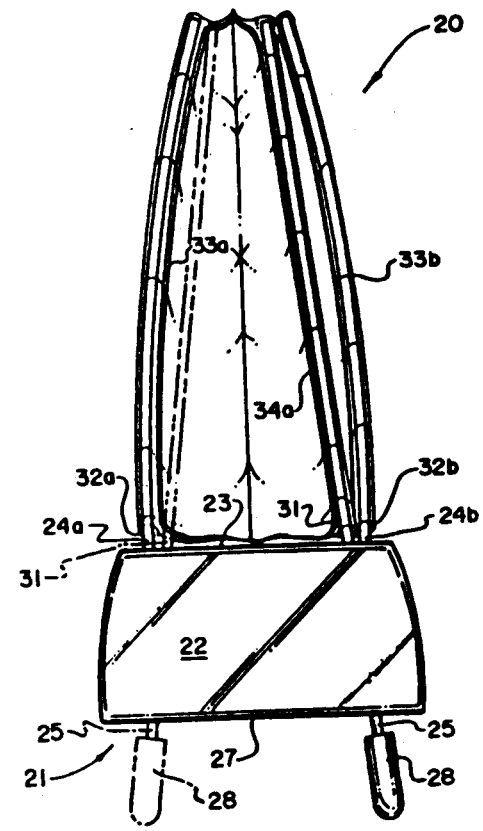
FIG. 6 is a top plan view of the urine collection system of FIG. 4, the siding center rod and flexible bag center sleeve shown resting against a right side of a longitudinal slot through the mount with the left flexible bag mouth shown open and, in broken lines, the sliding center rod and sleeve are shown moved to the left side of the longitudinal slot, closing the left flexible bag mouth and opening the right flexible bag mouth.

FIGS. 4 through 6 show a second embodiment of a urine collection system 20, herein after referred to as collector. Collector 20, like collector 10 is for use for collecting a urine specimen from a female. With, in this embodiment, collection of separate specimens provided for in a single evacuation.

Collector 20, as shown in FIGS. 4 through 6, includes a mount 21 that, like mount 11, also includes a hand engaging rectangular block 22. From a forward face or side 23 of which block identical co-planar outside flexible bag mounting rods 24a and 24b extend, that are hereinafter referred to as outside rods. The rectangular block 22 is wider than rectangular block 11 to appropriately space apart outside rods 24a and 24b so as to accommodate two flexible bags that are hung therebetween, are joined in side by side relationship and are connected along a common mouth edge, as set out hereinbelow. A straight sliding rod 25 is shown to extend through and beyond a lateral slot 26 that is formed through the rectangular block, which lateral slot is parallel to and equidistant from the top and bottom faces thereof. The sliding rod 25 is shown to extend from the slot 26 beyond the block forward and rear faces or sides 23 and 27, respectively. The sliding rod 25 extension from rectangular block forward face or side 23 is between and co-planar to the outside rods 24a and 24b. The opposite sliding rod end extends beyond the rectangular block rear face or side 27 and includes a cap 28 mounted to its end. Cap 28 prohibits the sliding rod 25 from being pulled away from the block forward face or side 23 and out of slot 26. Cap 28 is preferably an elongate closed cylinder for ease of manipulation by a female, who holds the rectangular block 22 in one hand and, with the fingers of her other hand, moves the cap end of sliding rod 25 from one side of slot 26 to the other, as shown in solid and broken lines in FIG. 6, and as set out below.

As shown in FIGS. 4 through 6, additional to mount 21, the collector 20 also includes a pair of identical flexible bags 29a and 29b that, like flexible bag 16, are each formed of a plastic material, and are joined along a common mouth edge 30, below a center sleeve 31. The two bags 29a and 29b are thereby maintained alongside one another, and the common mouth edge includes the center sleeve 31 that is to receive, as shown best in FIGS. 4 and 6, the sliding rod 25 fitted therealong. Sleeve 32a and 32b are provided along the outside edges of the individual flexible bags 29a and 29b, respectively, for receiving the outside rods 24a and 24b telescoped therein. The outside rods 24a and 24b, like rods 14a and 14b, are preferably bowed apart for providing a spreading apart of each of the flexible bag mouth ends, for positioning as illustrated in FIG. 2.

In practice, as illustrated in FIG. 6, the sliding rod 25 is initially positioned to a right side or end of slot 26, shown in solid lines, thereby opening wide the mouth of flexible bag 29a, with the mouth of flexible bag 29b closed. During use, the sliding rod 25 is moved across the slot 26, to the attitude shown in broken lines, thereby opening the mouth end of the other flexible bag 29b and closing the mouth end of flexible bag 29a. So operated, in one evacuation, both flexible bags will receive specimens therein. The connected flexible bags can then be simultaneously pulled off from the outside rods 24a and 24b and the sliding rod 25. The flexible bags are then individually sealed, preferably utilizing a ZIP LOCK™ type seal that is operated by pressing together slot sides 33a and 33b into ridges 34a and 34b of each of the flexible bags. The preferred seal is like that described for collector 10, and provides for individually sealing each of the flexible bags.

Where a type of plastic bag commonly known as a sandwich bag that utilizes a ZIP LOCK™ closure, has been successfully utilized as flexible bags 16, 29a and 29b, it should be understood that another flexible bag with different closure, utilized as described, could be incorporated into the invention within the scope of this disclosure. Also, it should be understood, the described mounts 11 and 21, that include rods 14a, 14b, 24a, 24b and 25 are preferably formed of a material or materials such as plastic, metal or the like, that is suitable for cleaning or sterilization between uses. Further, it should be understood, that while the present invention has been shown and described for use by a female for collecting a urine sample or samples for medical purposes, the collector 10 could also be used in a setting where a toilet facility is not conveniently available. As, for example, in a flight in a light aircraft without toilet facilities. For such use, the flexible bag should be of such size to contain and seal a significant volume of liquid to be disposed of after landing.

While preferred embodiments of the present invention have been shown and described herein, it should be understood that the present disclosure is made by way of example only and that variations thereto are possible without departing from the subject matter and reasonable equivalency thereof coming within the scope of the following claims, which claims I regard as my invention.

I claim:

1. A urine collection system comprising, a mount that includes a hand engaging means, from a front face of which mount co-planar rod means extend outwardly that are centrally bowed apart and slope towards one another to their forward ends; a flexible bag means that includes an open top or mouth end with sleeves formed along opposite edges of said flexible bag means mouth end; and means for closing said flexible bag means mouth end.

2. A urine collection system as recited in claim 1, wherein the hand engaging means is a rectangular block.

3. A urine collection system as recited in claim 1, wherein the means for closing the mouth end of the flexible bag means is a press to close seal that consists of a slot that is formed along one flexible bag means mouth edge, and a ridge that is formed along the other flexible bag means mouth edge that is to fit and bind in said slot.

4. A urine collection system as recited in claim 3, wherein the flexible bag means is formed form a pair of identical thin plastic sheets that are bonded together along their sides and across their bottom ends; and the sleeves are spaced apart from, alongside, and above the, respective, press to close seal slot and ridge.

5. A urine collection system as recited in claim 1, further including a center rod for arrangement through a slot that is formed through the mount hand engaging means, and said slot and center rod are co-planar to and located between the rod means, with an end of said center rod extending outwardly from a rear face of said mount hand engaging means, said center rod portion extending from said mount hand engaging means is approximately equal in length and co-planar to said rod means and said center rod and rod means are to receive sleeves of the flexible bag means fitted thereover; and said flexible bag means consists of a pair of identical flexible bags, each having an open mouth end, which flexible bags are joined along a common edge of their open mouth ends, below a center sleeve.

6. A urine collection system as recited in claim 5, further including a means for individually closing each said flexible bag mouth end.

7. A urine collection system as recited in claim 6, wherein the means for closing each said flexible bag mouth end is a press to close seal that consists of a slot that is formed along a mouth edge of each said flexible bag, and a ridge that is formed along an opposite mouth edge of each said flexible bag, said ridge to fit and bind in said slot.

8. A urine collection system as recited in claim 7, wherein each flexible bag means is formed from a pair of identical thin plastic sheets that are bonded together along their sides and across their bottom ends, and are joined at their common mouth end edges with the center sleeve formed thereabove.

* * * * *